US012716882B2

(12) United States Patent
Qahtani et al.

(10) Patent No.: US 12,716,882 B2
(45) Date of Patent: Aug. 25, 2026

(54) ROBOTIC DEVICE AND METHOD FOR GATHERING SOIL DATA ALONG PIPELINES USING SMART SENSORS

(71) Applicant: Saudi Arabian Oil Company, Dhahran (SA)

(72) Inventors: Ghazi Salman Qahtani, Khobar (SA); Rahaf Nasser Almutairi, Dhahran (SA); Maher Hamed Alerwi, Dhahran (SA); Christian Canto Maya, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 530 days.

(21) Appl. No.: 18/179,733

(22) Filed: Mar. 7, 2023

(65) Prior Publication Data

US 2024/0302343 A1 Sep. 12, 2024

(51) Int. Cl.

*G01N 33/24* (2006.01)
*G01N 27/416* (2006.01)
*G05D 1/00* (2024.01)

(52) U.S. Cl.

CPC ......... *G01N 33/24* (2013.01); *G01N 27/4166* (2013.01); *G01N 27/4167* (2013.01); *G05D 1/0278* (2013.01)

(58) Field of Classification Search

CPC ............... G01N 33/24; G01N 27/4166; G01N 27/4167; G01N 33/245; G05D 1/0278

See application file for complete search history.

(56) References Cited

U.S. PATENT DOCUMENTS

| | | | |
|---|---|---|---|
| 7,944,220 | B2 | 5/2011 | Lock |
| 9,585,307 | B2 | 3/2017 | Holland |
| 9,864,094 | B2 | 1/2018 | Stoller et al. |
| 10,321,623 | B1 | 6/2019 | Maxton et al. |

(Continued)

FOREIGN PATENT DOCUMENTS

| | | |
|---|---|---|
| CN | 108279211 A | 7/2018 |

OTHER PUBLICATIONS

Nikolov, et. al., "Soil Moisture Measurement with Flexible Sensors", Proc. XXIX International Scientific Conference Electronics—ET2020, Sep. 16-18, 2020, Sozopol, Bulgaria (Year: 2020).*

(Continued)

*Primary Examiner* — Catherine T. Rastovski
*Assistant Examiner* — Toni D Sauncy
(74) *Attorney, Agent, or Firm* — Leason Ellis LLP

(57) ABSTRACT

An apparatus for gathering soil data along a trajectory comprises a crawler body that houses a processor that is configured with instructions for controlling the apparatus, memory coupled to the processor, and a GPS module and motor also coupled to the processor. The apparatus also includes a pair of continuous tracks coupled to the crawler body and rotatable through a coupling with the motor, wherein the continuous tracks include planar sections, one or more of the planar sections including a plurality of flexible smart sensors that are each configured to detect and store data concerning at least one property or condition of the soil when the apparatus moves over the soil along the trajectory. The flexible smart sensors are resilient when subjected to bending forces when the continuous tracks move along the soil.

12 Claims, 5 Drawing Sheets

(56) References Cited

U.S. PATENT DOCUMENTS

| | | | | |
|---|---|---|---|---|
| 2015/0204041 | A1* | 7/2015 | Chang | H04W 4/70 702/2 |
| 2021/0309308 | A1* | 10/2021 | Sauvageau | B62D 55/14 |

OTHER PUBLICATIONS

CN107860892_EnglishTranslation (Pe2E (Year: 2018).*

Gao, et. al., "Design and Test of a Soil Profile Moisture Sensor Based on Sensitive Soil Layers", Special Issue Smart Sensors for Water Systems and Networks, Published: May 21, 2018 (Year: 2018).*

Hassan, et. al., "Towards technological adaptation of advanced farming through AI, IoT, and Robotics: A Comprehensive overview", Accepted Manuscript of a book chapter published by Routledge/CRC Press in [Artificial Intelligence and Smart Agriculture Technology on (Jun. 27, 2022) (Year: 2022).*

Kitic, et. al., 'Agrobot Lala' An Autonomous Robotic System for Real-Time, In-Field Soil Sampling, and Analysis of Nitratesâ, Sensors 2022, 22, 4207. (Year: 2022).*

Patil, et. al. "Monitoring soil pH variation using Polyaniline/SU-8 composite film based conductometric microsensor" Sensors & Actuators: B. Chemical 286 (2019) 583-590 (Year: 2019).*

Rayhana , et. al., "Printed Sensor Technologies for Monitoring Applications in Smart Farming: A Review", IEEE Transactions on Instrumentation and Measurement, vol. 70, 2021 (Year: 2019).*

Zhang, et. al.,("A Smart Robotic System for Non-Contact Condition Monitoring and Fault Detection in Buried Pipelines", paper presented at the Abu Dhabi International Petroleum Exhibition & Conference held in Abu Dhabi, UAE, Nov. 12-15, 2018.) (Year: 2018).*

Pobkrut, Theerapat et al.; Soil sensing survey robots based on electronic nose; 2014 14th International Conference on Control, Automation and Systems; Oct. 22-25, 2014; Korea; 7 pages.

Adamchuk, V.I. et al; On-the-go soil sensors for precision agriculture; Computers and Electronics in Agriculture 44, 2004; 71-91.

Anindya Nag et al.; Wearable Flexible Sensors: A Review, IEEE Sensors Journal, vol. 17, No., 13, Jul. 1, 2017; 12 pages.

Bouchaib Zazoum et al.; Recent Advances in Flexible Sensors and Their Applications; Sensors 2022, 22, 4653.; https://doi.org/10.3390/s22124653; Jun. 20, 2022; 17 pages.

Yongmin He et al.; An Overview of carbon materials for flexible electrochemical capacitors; The Royal Society of Chemistry; Nanoscale, 2013, 5, 8799; Jul. 25, 2013; 23 pages.

Nyabadza, A. et al.; Flexible sensors, fabrication and materials; E Scholary Community Encyclopedia; https://encyclopedia.pub/entry/14491; Downloaded Jan. 18, 2023.

Sehrawat et al. "Smart sensors: Analysis of different types of IoT sensors." 2019 3rd International Conference on Trends in Electronics and Informatics (ICOEI). IEEE, 2019. 6 pages.

Saudi Arabian Office Action of application #SA1020240876, dated Nov. 18, 2025, including translation. 17 pages.

Zhang et al. "A Smart Robotic System for Non-Contact Condition Monitoring and Fault Detection in Buried Pipelines", paper presented at the Abu Dhabi International Petroleum Exhibition & Conference held in Abu Dhabi, UAE, Nov. 12-15, 2018. (Year: 2018). 14 pages.

Zhang et al. "Predict the Rover Mobility Over Soft Terrain Using Articulated Wheeled Bevameter," in IEEE Robotics and Automation Letters, vol. 7, No. 4, pp. 12062-12069, Oct. 2022, doi: 10.1109/LRA.2022.3211153. 9 pages.

* cited by examiner 120
220
215
222
210
212
205
235
240
242
225
232
230
125

400
410
420
H2O
H2O
H2O+
H2O

ROBOTIC DEVICE AND METHOD FOR GATHERING SOIL DATA ALONG PIPELINES USING SMART SENSORS

FIELD OF THE DISCLOSURE

The present disclosure relates to corrosion detection and, more particularly, relates to a robotic device and method that is used for gathering soil data long pipelines using smart sensors to assess how such soil conditions affect rates of pipeline corrosion.

BACKGROUND OF THE DISCLOSURE

The oil and gas industry deploys vast amounts of pipeline infrastructure for fuel transport. The pipelines are subject to corrosion due to the fuels transported, the material composition of pipes, and the environment in which the pipelines are placed or embedded. This is particularly true for underground pipes, for which soil conditions can lead to accelerated corrosion.

To better understand how soil conditions affect corrosion mechanisms it is important to gather as much information as possible about the soil properties along the pipelines and the influence of the soil properties on observed pipelines. Research in the field has shown that numerous variables including resistivity, humidity, soil chemistry, redox potential, pH, bacterial activity, among others can greatly influence the aggressiveness of the external corrosion.

In the agricultural field, there are robotic rover systems equipped with sensors that travel along a path while taking data from soil samples at increments along the path. Typically such systems use sensors and detectors that penetrate the soil to assess soil conditions at various depths. While these systems are useful for some applications, they are not tailored to gather a wide spectrum of soil condition data in a rapid and efficient manner, as required for assessing pipeline corrosion.

What is therefore needed is a robust and efficient robotic system that can gather comprehensive and high-resolution soil condition data rapidly so as to cover pipeline infrastructure installations.

SUMMARY OF THE DISCLOSURE

The present disclosure provides, in one aspect, an apparatus for gathering soil data along a trajectory. The crawler comprises a crawler body that houses a processor that is configured with instructions for controlling the apparatus, memory, GPS and a motor coupled to the processor, and a pair of continuous tracks coupled to the crawler body and rotatable through a coupling with the motor, the continuous tracks including planar sections. A plurality of flexible smart sensors that are each embedded in one of the planar sections are configured to detect and store data concerning at least one property or condition of the soil when the apparatus moves over the soil along the trajectory, the plurality of flexible smart sensors being provided on one or more of the planar sections. The flexible smart sensors are resilient when subjected to bending forces when the continuous tracks move along the soil.

In another aspect, the present disclosure provides a method of gathering soil data along a trajectory. The method includes configuring a crawler apparatus having a body that houses a processor that is configured with instructions for controlling the apparatus, memory, a GPS module and a motor coupled to the processor to move automatically along the trajectory. The method further includes obtaining soil data via a plurality of flexible smart sensors included in a pair of continuous tracks coupled to the crawler body and rotatable through a coupling with the motor, the continuous tracks including planar sections that hold the plurality of flexible smart sensors that are each configured to detect and store data concerning at least one property or condition of the soil when the apparatus moves over the soil along the trajectory, wherein the flexible smart sensors are resilient when subjected to bending forces when the continuous tracks move along the soil. The obtained soil data are transmitted from the flexible sensors for storage.

These and other aspects, features, and advantages can be appreciated from the following description of certain embodiments and the accompanying drawing figures and claims.

DETAILED DESCRIPTION OF CERTAIN EMBODIMENTS OF THE DISCLOSURE

The present disclosure provides an apparatus that monitors soil conditions along a path for the main purpose of assessing the soil for corrosive properties. The apparatus is an unmanned roving vehicle (hereinafter termed a "crawler") that is capable of roving over the soil above a buried pipeline. The crawler is guided using a GPS module that provides coordination with the known location of the pipeline and enables the crawler to travel along a predetermined trajectory. The crawler includes a suite of sensors that are configured to detect and gather data regarding soil properties such as but not limited to: soil chemistry, humidity, resistivity, soil redox potential, bacterial content, and pH. The sensors are fabricated using flexible materials so that they can be positioned and aligned on the track of the crawler (such as a caterpillar tread). This allows collection of soil condition data directly on the path that the crawler is moving along the soil on top of the pipeline. In preferred embodiments, the sensors are "smart" sensors that can transmit sensor data directly, in real time, to a data center via a communication network.

Figure 1:
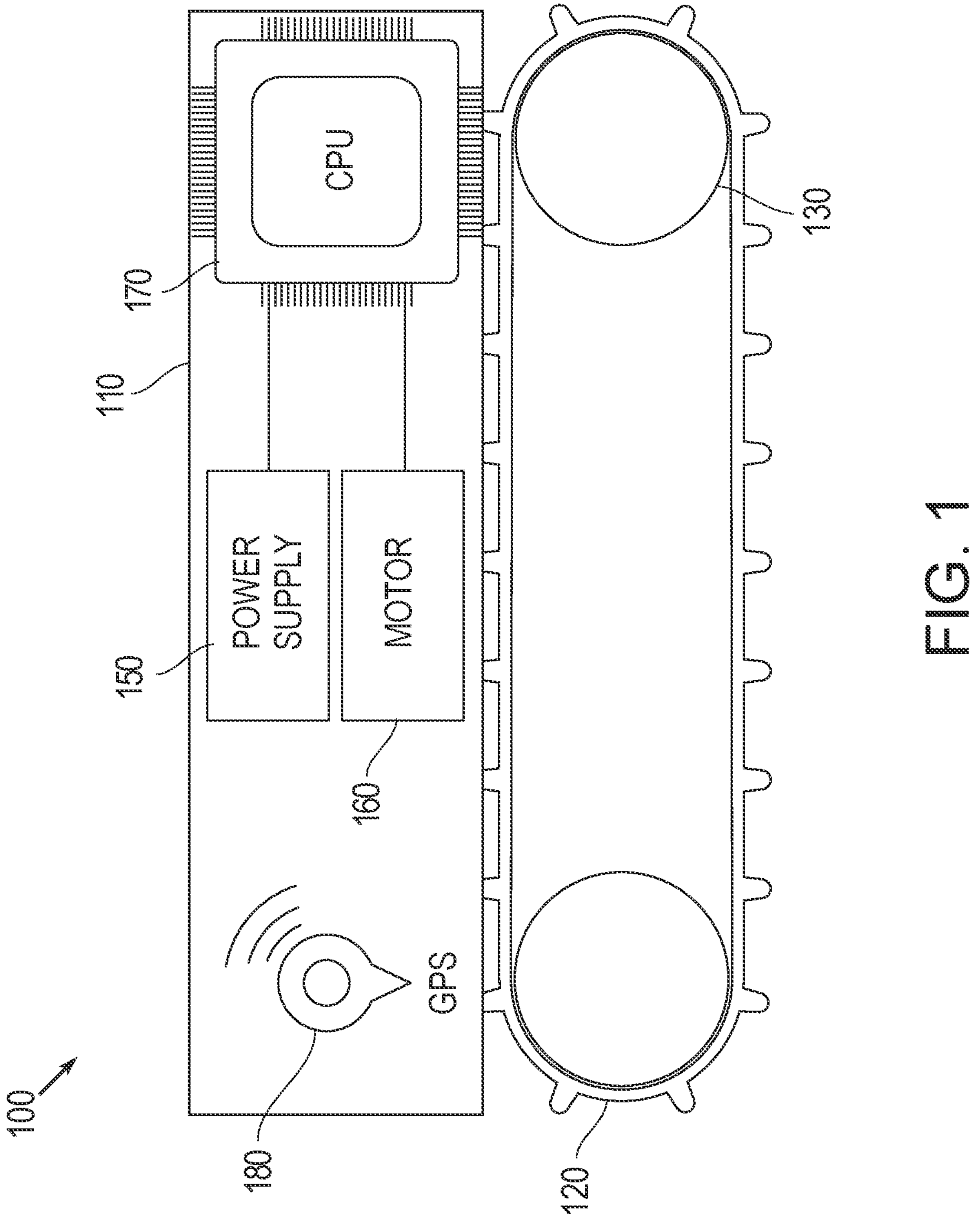
FIG. 1 is a schematic side view of an embodiment of a crawler according to the present disclosure.

FIG. 1 is a schematic side view of an embodiment of the crawler according to the present disclosure. The crawler 100 includes a body 110 the contains electronic and other components powering and controlling the crawler. The crawler 100 also includes a continuous caterpillar track or belt 120 (only one track is shown in the side view) that is fitted over a plurality of rollers (e.g., sprockets) 130. The body of the crawler 110 houses a power supply 150, motor 160, processor 170 a GPS module 180, and a communication module (not shown in FIG. 1) with wireless communication capability as will be discussed further below with respect to the system embodiment. The movement of the crawler 100 can be controlled by a remote operator by wireless communications. The crawler can also operate automatically based on preset instructions.

Figure 2:
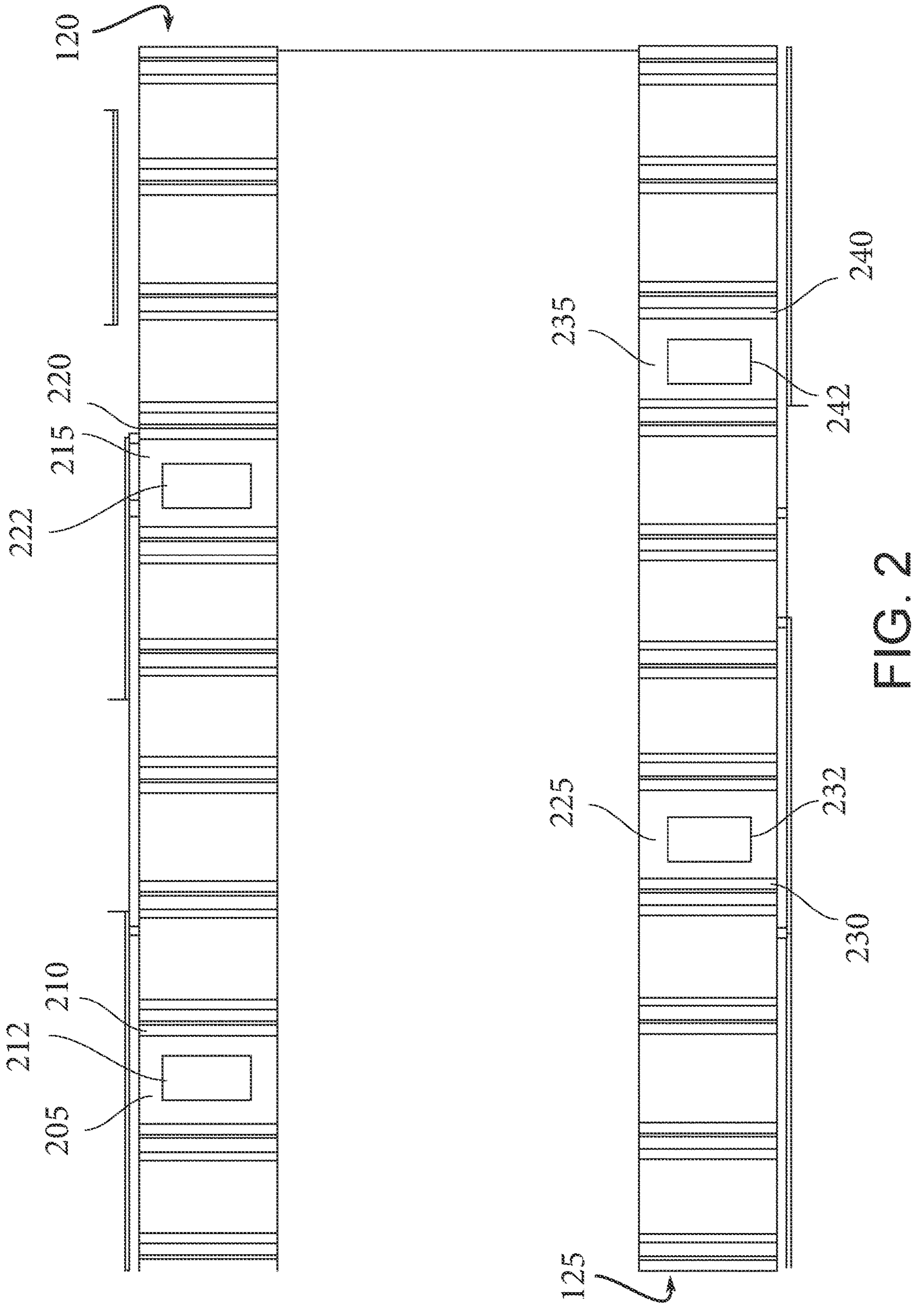
FIG. 2 is a schematic bottom view of the crawler 100 that shows both caterpillar tracks and their components.

FIG. 2 is a schematic bottom view of the crawler 100 that shows both caterpillar tracks and their components. A first track 120 includes substantially planar belt elements, e.g., 205, 215 that alternate with respective tread elements, e.g., 210, 220, that divide and separate the planar belt elements from each other. A second track 125, positioned on the opposite side of the crawler, includes additional substantially planar belt elements, e.g., 225, 235 that alternative with respective tread elements 230, 240. The tread elements e.g., 210, 220, 230, 240 provide a degree of traction as they protrude from the caterpillar tracks and exert pressure on the ground surface as the track rotates and the crawler is moved. One or more of the belt elements, and preferably, a plurality of the belt elements 205-235, contain flexible sensors e.g., 212, 222, 232, 242 that can be used to detect and record soil condition data in real time as they come into contact with the ground surface through rotation of the tracks. Preferably, the sensors are "smart sensors" as are known in the art. In addition to their ability to measure parameters in the physical environment, smart sensors include additional computing resources that enables the sensors to process the received measurements as well communicate the processed data in real-time to other resources. As each smart sensor can be uniquely identified, such as with an RFID, the sensors can participate as element in an internet of things (IOT) network.

More particularly, the flexible smart sensors with which the crawler is equipped are designed to capture soil condition data including, but not necessarily limited to, electrical properties such as soil resistivity, conductivity and redox potential, chemical properties including the presence of selected gases, pH and moisture, as well as general physical conditions such as temperature and density. Robust, flexible sensors that can be used to measure each of these properties, either alone, or in some cases in combination, have been developed recently and these sensors can be embedded or implanted in the belt elements of the caterpillar track. Typically, in order for the flexible sensors to detect the various soil conditions, there must be some contact between the soil and the sensors, and therefore the active portions of the sensors cannot be completely encapsulated within the material caterpillar track (e.g., rubber or other elastomeric materials). There are different techniques for ensuring such sensor-soil interfacing. In some embodiments, the components of the sensor can be fabricated directly onto the surface of the belt elements of the track. in other embodiments, the components of the sensors can be embedded in the material of the track so that there is no direct contact between the components and the soil. In such implementations, microscopic pores can be punctured into the bottom surface of the belt elements to create pathways for detecting analytes, allowing the sensors to detect soil conditions.

Over the past decade a significant amount of research has been conducted in developing sensors that are sensitive, robust and flexible (and even wearable). There are now a number of different fabrication techniques and substrate materials that can be used to make flexible sensors. One group of techniques involves the deposition of thin functional layers on elastomeric substrates such as plastics. Some of the substrates that have been used for this include polydimethysiloxane (PDMS), polyethylene naphthalate (PEN), polyethylene terephthalate (PET), polyimide (PI), parylene, polypyrrole. The active (conductive or semiconductive) portions or layers of the sensors can be composed of graphene, carbon nanotubes, carbon fibers, silver, gold, nickel nanoparticles, or fluid conductive inks. The active layers can be added by photolithography, screen-printing, screen-printing or inkjet printing.

Figure 3A:
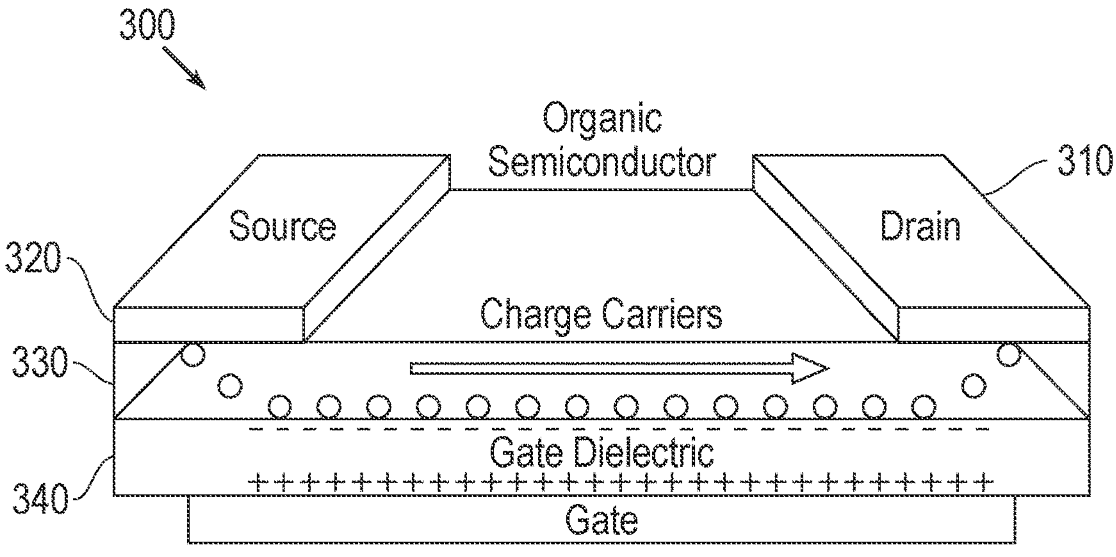
FIG. 3A shows a schematic cross-sectional view of an example flexible FET-based sensor.
Figure 3B:
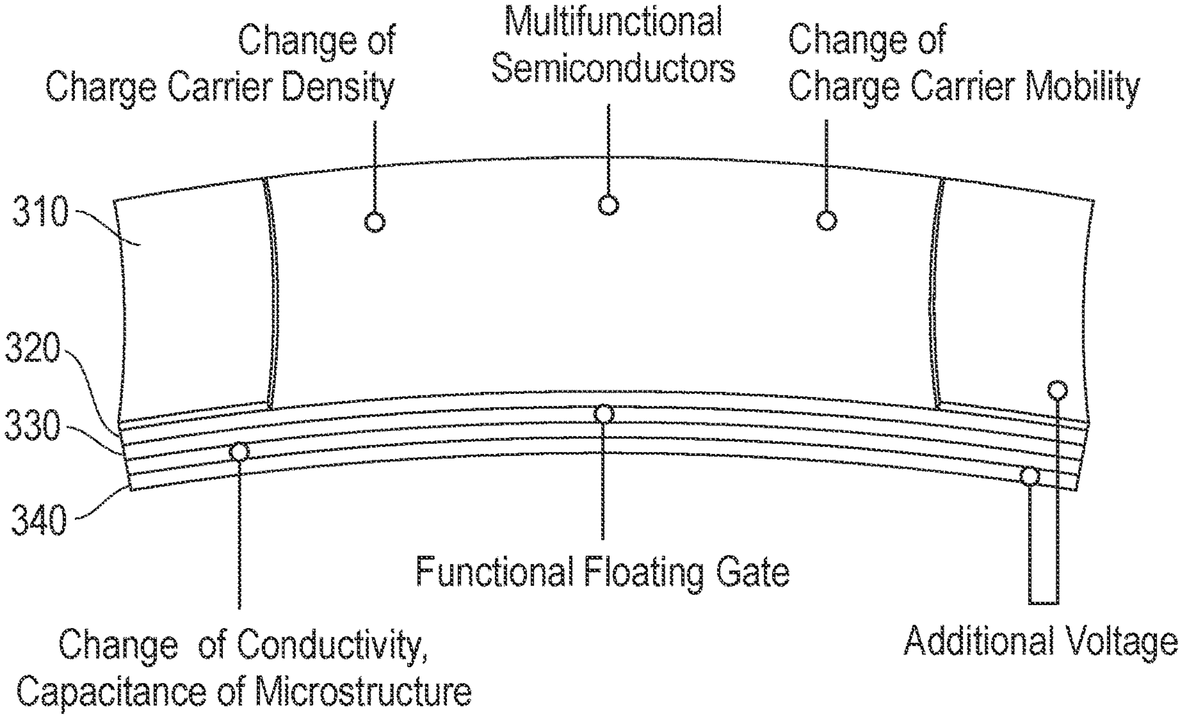
FIG. 3B is an illustration of the bending of the flexible sensor shown in FIG. 3A under pressure.

The transduction methods of the plurality of flexible sensors can vary widely. Pressure sensors can utilize piezoconductivity, piezoresistivity, as well as changes in capacitance, impedance and voltage. Other types of sensors rely on the electrical properties of organic semiconductors. Flexible sensors based on field-effect transistors (FET) have variable conduction that can be used for a wide variety of applications including chemical species or pH detection, and also as pressure, temperature and optical sensors. FET-based transistors have the advantage of high sensitivity due to amplification. FIG. 3A shows a schematic cross-sectional view of an example flexible FET-based sensor that can be used in the apparatus and methods of the present disclosure. The sensor 300 is a multi-level structure containing (from upper to lower) an upper terminal layer 310 consisting of a source electrode and a drain electrode, an active layer 320 beneath the upper terminal layer is typically a thin film formed of a semi-conductive and typically semi-porous material based on the target analyte, such as, but not limited to graphene pentacene, Indium Tin Oxide (InZO). Tungsten Trioxide ($WO_3$), Ruthenium Oxide ($RuO_x$), and carbon nanotubes. A dielectric layer 330 is positioned beneath the active semiconductor layer and a lower terminal layer 340 consisting of a gate electrode is the lower layer. The dielectric layer selected is dependent upon the active layer material but is typically a flexible and non-conductive polymeric material. The dielectric material can be modified for a suitable interface with the active layer. In operation, an electrical current flows from the source to the drain terminal through the underlying active layer 320. The magnitude of the source-drain current is tuned by a voltage that is applied to the lower terminal layer (at the gate). When the flexible FET sensor is exposed to the external environment, such as a soil sample, the electrical characteristic of the active layer is changed by trapping target analytes. Properties of the electrodes can also be altered to provide further sensing activity. FIG. 3B is an illustration of the bending of the flexible sensor shown in FIG. 3A under pressure. The thin film structure is resilient and function of the sensor is unimpaired by stressing the sensor in this manner.

Flexible humidity sensors can utilize the adsorbtion of water molecules on active layers having hydroxyl groups and/or surface defects. In the presence of an electrostatic field, the water molecules are easily ionized and hydronium ions ($H_3O^+$) are spontaneously generated and transferred by proton-hopping among adjacent water molecules. There are a number of methods that can be used to measure this effect. One prevalent technique is direct-current (DC) mode in which adsorption of the proton-hopping water molecules induces changes in resistance or conductance. Electronic conductive materials such as Zinc indium sulfide ($ZnIn_2S_4$; ZIS) can be used as the active layer since it has been found that the semiconductive properties of ZIS change in the presence of the proton-hopping of water/hydronium molecules. Ionic conductive materials such as, for example, organohydrogels are designed to respond directly to changes in the ionic current mediated by potassium and calcium ions that reduce in concentration with a decrease in relative humidity.

Another transduction technique is based on capacitance changes. Flexible sensors that use this technique can be structured in layers with two planar electrodes and an intermediate sensor layer. The capacitance change is induced by the variation of dielectric constant (8) of the sensing layer when it is exposed to water. Impedance-type flexible humidity sensors have also been widely investigated. Impedance generally decreases with increase in relative humidity and operation frequency. The flexible humidity sensors do not necessarily need an external voltage source (small though the required voltage usually is, on the order of millivolts). Electricity can be generated when water molecules interact with active materials either by streaming current, or ion concentration gradient.

As noted above, the active layer can be made using a variety of inorganic nanomaterials, graphene and its derivatives (graphene oxide (GO) and reduced graphene oxide (rGO)), metal sulfides and metal oxides. The active layers of flexible sensors can be fabricated using various deposition methods to support active sites, such as defects, vacancies and hydrophilic groups on their surfaces that promote the capture of water molecules. For example, Craciun et al, in "Water-based solution processing and wafer-scale integration of all-graphene humidity sensors" Adv. Sci. 6(15) (2019), demonstrated a graphene based humidity sensor in a silicon and PET substrate. In addition, certain polymers can also be used to form the active layer. Conductive or semi-conductive polymers that are linked to functional groups such as COOH, OH, and $NO_2$ form hydrogen bonds with water molecules. The polymer chosen for a specific flexible sensor can be selected based on electron or ionic conductivity. Electron-conductive polymers typically have long chains in which electrons can migrate along the chain via double bonds. Such electron-conductive polymers include polyaniline (PANI), polypyrrole (PPy) and polythiophene (PEDOT). In contrast, ion-conductive polymers transport ion current using ionic liquids combined with aqueous electrolytes such as KCl, KOH or $CoCl_2$. In one example, an ionic polymer film consisting of polyvinylidene fluoride (PVDF) and 1-butyl-3-methylimidazolium-tetrachloroferrateionic liquid has been used for humidity sensing applications. Upon incorporating the ionic liquid with PVDF, the frequency dependent dielectric constant goes up along with the increasing content of ionic liquid, leading to enhancement of electronic conductivity.

Figure 4:
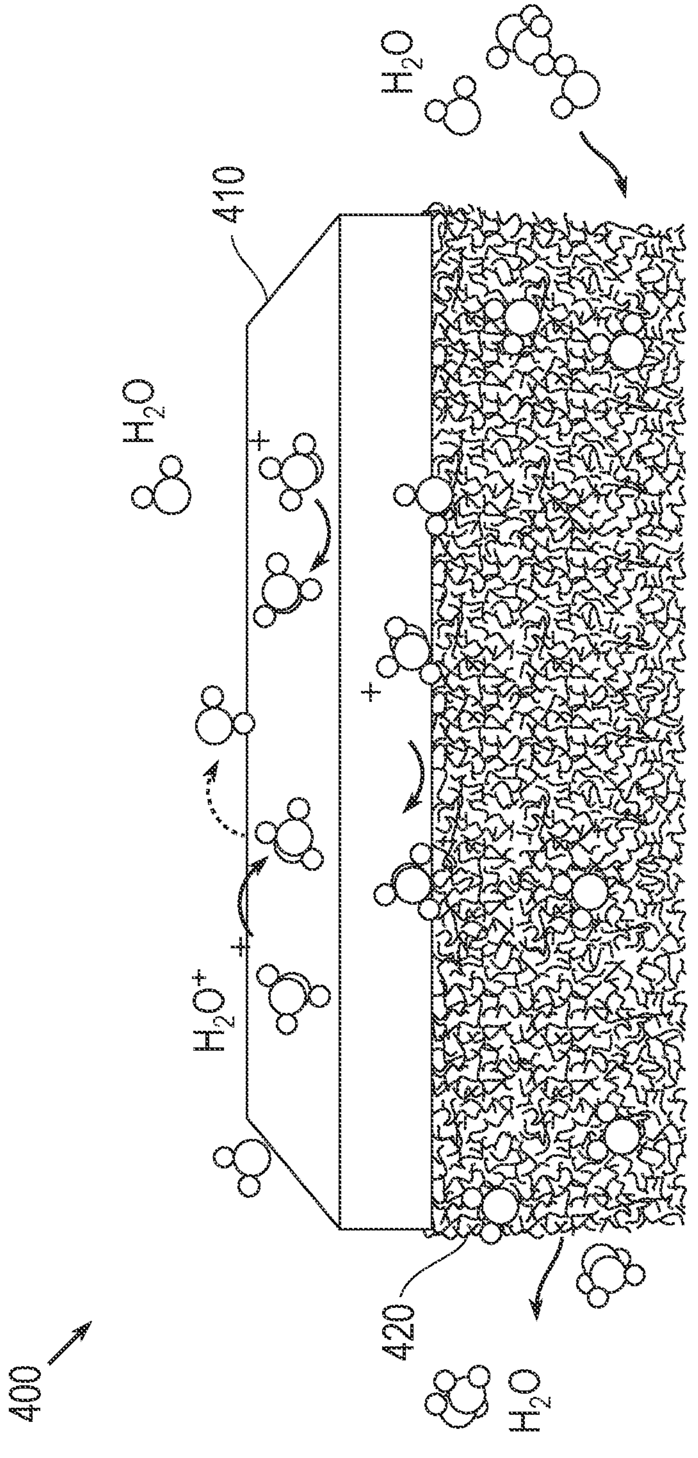
FIG. 4 shows an example section of a flexible humidity sensor that can be used in the crawler of the present disclosure.

The sensitivity and accuracy of the flexible humidity sensors are improved by engineering active sensing materials or electrodes into porous structures. For example, laser induced graphene (LIG) is a useful material due to its high-density, which promote sufficient absorption and desorption of water molecules. Deposition of $ZnIn_2S_4$ nanosheets as active sensing materials onto the LIG electrodes allows the formation of a highly stable humidity sensor. FIG. 4 shows an example section of a flexible humidity sensor that can be used in the crawler of the present disclosure that based on an LIG-$ZnIn_2S_4$ active layer. As shown, the sensor 400 includes a layer of $ZnIn_2S_4$ 410 which is hydrophilic, deposited over a porous LIG layer 420.

The flexible sensors described above embodiments are exemplary and many other designs and combinations of substrates and active portions can be used to produce flexible that can be used in various embodiments the crawler described herein. Different materials and transduction techniques can be used based on the parameter being detected. For example, temperature and soil texture measurements can use different modalities based on changes in electrical properties in various materials upon changes in temperature.

TABLE I, shown below, lists types of flexible sensors in terms of their mode of detection together with the agronomic soil properties that they are suited to detect and/or measure through a signal output. The sensor types include electrical and electromagnetic, optical and radiometric, mechanical, acoustic and pneumatic and electrochemical. Each of these types is implemented using flexible sensor technology. For example, ultrasound (acoustic) transducers can be fabricated on thin films using materials similar to those described above. As indicated in the table, electrical and electromagnetic sensors are suited for detecting soil texture, content, solidity and bulk density. Electrochemical sensors, some of which were described above are suited for detecting soil pH, nitrogen and other nutrients. Optical and radiometric sensors, on the other hand, are suited for detecting density and depth variability. Preferably, the crawler is equipped with all, or a plurality of the different types of sensors to obtain coverage of as many of the agronomic soil properties as possible. It is noted that flexible electrochemical sensors can also be used to detect relative humidity (moisture) as described above with respect to FIG. 4.

TABLE I

| | Agronomic soil properties | | | | | | | | | |
|---|---|---|---|---|---|---|---|---|---|---|
| Sensors | Soil texture (clay, silt and sand content) | Soil organic matter or total carbon content | Soil moisture content | Soil salinity or sodium content | Soil compaction Or bulk density | Depth variability (depth of topsoil or hard pan detection) | Soil pH | Residual nitrate or total nitrogen content | Other macronutrients (i.e. potassium content) | Cation exchange capacity and other buffer indicators |
| Electrical and electromagnetic | Yes | Yes | Yes | Yes | N/A | Yes | N/A | Yes | N/A | Yes |
| Optical and radiometric | Yes | Yes | Yes | N/A | N/A | N/A | Yes | Yes | N/A | Yes |
| Mechanical | N/A | N/A | N/A | N/A | Yes | Yes | N/A | N/A | N/A | N/A |
| Acoustic and pneumatic | Yes | N/A | N/A | N/A | Yes | Yes | N/A | N/A | N/A | N/A |
| Electrochemical | N/A | N/A | N/A | Yes | N/A | N/A | Yes | Yes | Yes | N/A |

Figure 5:
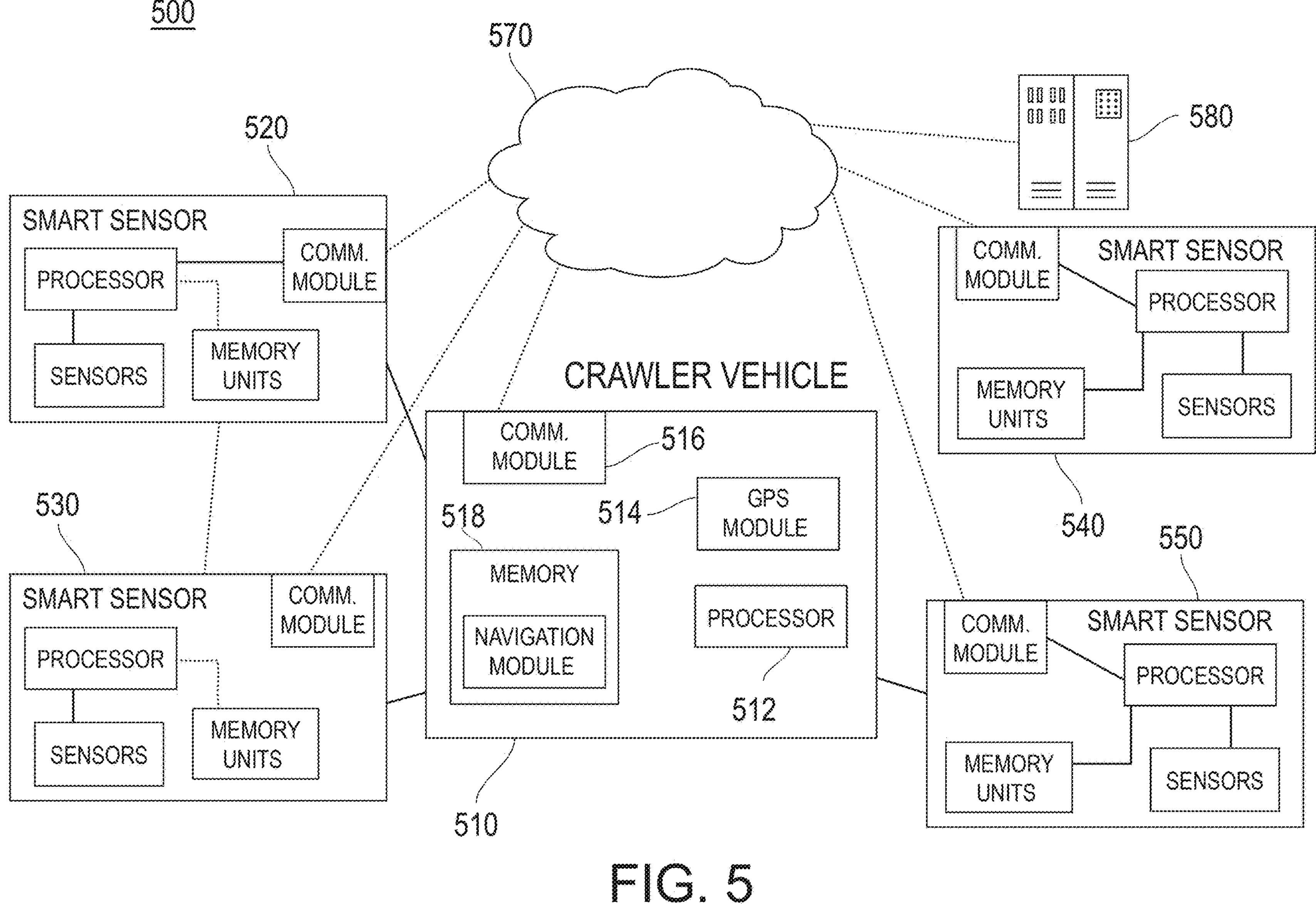
FIG. 5 is a schematic block diagram of a functional system of a crawler according to an embodiment of the present disclosure.

FIG. 5 is a schematic block diagram of a functional system of a crawler according to an embodiment of the present disclosure. The system 500 includes the crawler vehicle body 510 which is directly or indirectly coupled (for example, by electric wire or wireless communication) to a plurality of smart sensor 520, 530, 540, 550 which are positioned in the tracks of the crawler. Although four smart sensors are shown, this is arbitrary, and a larger number of sensors can be incorporated in the system (or in some cases, a smaller number as well). The crawler body 510 houses a processor 512, and several modules coupled to the processor 512 including a GPS module 514, a communications module 516 and a memory unit 518. The memory unit can store an on-board navigation program module that can be used to activate, stop and guide the vehicle during soil testing investigations. The processor 512 can be a general central processing unit (CPU) type processor or can be a more specialized unit tailored to the crawler. The memory unit 518 can include readable media in the form of volatile memory, such as random access memory (RAM) and/or cache memory.

Each of the smart sensors 520-550 include one or more flexible sensor devices as described above for detecting properties of the soil as the crawler travels. The smart sensors 520-550 also each include a processor, such as a digital motion processor, local memory and a communication module. Due to their processing capability and communication modules, the smart sensors 520-550 can receive input from external sources and use pre-built functions to detect specific inputs corresponding to the sensor devices that the contain. Preferably, the flexible smart sensors 520-550 are connected in an Internet of Things (IoT) network and are able to exchange data. The IoT is a system in which computing devices, and other devices equipped with processing capability are provided with unique identifiers and the ability to automatically transfer data over a network. Each of the smart sensors can include radio-frequency identification (RFID) tags that enables each sensor to be identified and tracked and associated with other objects. Due to their unique identifiers, a computing system that communicates with a given sensor, such as the processor of the crawler or an external data center, can identify the source of the information. Additionally, since the crawler is equipped with a GPS, the location of the sensors can also be tracked to within millimeter accuracy. Within the IoT, various devices can communicate with each other and can access data from sources available over various communication networks 570, including the Internet. This system allows both collection and broadcast of data to a collection data center 580.

The crawler communication module 514 and sensor communication modules operate over a 510 one or more of short-range, digital data communication network 570. Examples of the network 570, but are not limited to, a wireless local area network (e.g., a wireless "LAN" or "WiFi" network), a RF network, a Near Field Communication (NFC) network, an optical communications network (e.g., a wireless infrared (IR) communications network, etc.), a Bluetooth™ communications network. Additionally, the local network can be a private or internal network, a wide area network (e.g., a "WAN," such as the Internet), and/or a publicly accessible network via one or more communication protocols, including, but not limited to, hypertext transfer protocol (HTTP), transmission control protocol/internet protocol (TCP/IP), extensible messaging and presence protocol (XMPP), message queuing telemetry transport (MQTT) protocols, constrained application protocol (CoAP), data distribution service (DDS) protocols, ZigBee™ communications protocols, and NFC protocols.

There are different ways in which the data obtained by the flexible sensors (also terms "sensor data" herein) can be stored. Data collected by a particular smart sensor can, in the first instance, be locally stored in memory contained in the sensor. Additionally or alternatively, the smart sensor can communicate the data to the crawler, which can act as a local data hub for the sensor data over a particular data collection run. The sensor data can also be sent via the communication network to a data center that is configured as a repository for soil condition data at pipeline infrastructure installations.

The crawler and combination of smart flexible sensors of the present disclosure provides the ability to measure the soil properties at any location along the path of a pipeline which offers the opportunity to minimize the failure due to external corrosion in long transmission pipelines, and to have a better monitoring assessment. Since soil corrosivity influences the aggressiveness of external corrosion, having a clearer knowledge and understanding of soil properties enhances the mitigation and monitoring assessments. The crawler can be automatically controlled GPS coordination without the need for the involvement of a human operator. The result of the investigation is a detailed mapping of the soil conditions at each minute interval along targeted pipelines It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components or steps described and illustrated with reference to the figures are required for all embodiments or arrangements.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and "comprising", when used in this specification, specify the presence of stated features, integers, steps, operations, elements, or components, but do not preclude the presence or addition of one or more other features, integers, steps, operations, elements, components, or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. An apparatus for gathering soil data along a trajectory comprising:

a crawler body that houses:

a processor that is configured with instructions for controlling the apparatus, memory coupled to the processor, a GPS module coupled to the processor, and a motor coupled to the processor;

a pair of continuous tracks coupled to the crawler body and rotatable through a coupling with the motor, the continuous tracks including planar sections; and a plurality of flexible smart sensors that are each embedded in one of the planar sections and are configured to detect and store data concerning at least one property or condition of the soil when the apparatus moves over the soil along the trajectory, the plurality of flexible smart sensors being provided on one or more of the planar sections, wherein at least two of the plurality of smart sensors are embedded in a first of the pair of continuous tracks, with one of the at least two sensors being embedded in one planar section of the first continuous track and another of the at least two sensors being embedded in another planar section of the first continuous track, and wherein another two of the plurality of sensors are embedded in a second of the pair of continuous tracks, with one of at the least two other sensors being embedded in one planar section of the second continuous track and another of the at least two sensors being embedded in another planar section of the second continuous track, wherein the flexible smart sensors are resilient when subjected to bending forces when the continuous tracks move along the soil.

2. The apparatus of claim 1, wherein the flexible smart sensors include at least one of: an electromagnetic sensor, an electrochemical sensor, an optical or radiometric sensor, an acoustic or pneumatic sensor, and a mechanical sensor.

3. The apparatus of claim 2, wherein the flexible sensors include an electrochemical sensor configured to detect soil pH.

4. The apparatus of claim 2, wherein the flexible sensors include an electrochemical sensor configured to detect relative humidity.

5. The apparatus of claim 2, wherein the flexible sensors include an electrochemical sensor configured to detect a specific target analyte within the soil.

6. The apparatus of claim 2, wherein the flexible sensors include an electromagnetic sensor configured to detect one or more of a texture of the soil, organic content, nitrogen content, relative humidity, and soil depth variability.

7. The apparatus of claim 2, wherein the flexible sensors include an acoustic or pneumatic sensor configured to detect soil compaction or bulk density.

8. The apparatus of claim 2, wherein the flexible sensors each include a local processor and a communication module in addition to a detector, and are configured to communicate sensor data via an Internet of Things (IoT) network using the communication module.

9. The apparatus of claim 8, wherein the flexible sensors communicate sensor data to the communication module of the crawler body where it is stored using the on-board memory of the crawler body.

10. The apparatus of claim 1, wherein the processor of the crawler is configured to send instructions so as to control the crawler to automatically travel along a trajectory that is determined by reference to geographical coordinates obtained using the GPS module.

11. The apparatus of claim 10, wherein the trajectory follows a path along soil over a buried pipeline.

12. A method of gathering soil data along a trajectory comprising:

configuring a crawler apparatus having a body that houses a processor that is configured with instructions for controlling the apparatus, memory, a GPS module and a motor coupled to the processor to move automatically along the trajectory;

obtaining soil data via a plurality of flexible smart sensors included in a pair of continuous tracks coupled to the crawler body and rotatable through a coupling with the motor, the continuous tracks including planar sections that hold the plurality of flexible smart sensors that are each configured to detect and store data concerning at least one property or condition of the soil when the apparatus moves over the soil along the trajectory, wherein the flexible smart sensors are resilient when subjected to bending forces when the continuous tracks move along the soil; and transmitting the obtained soil data from the flexible sensors for storage, wherein at least two of the plurality of smart sensors are embedded in a first of the pair of continuous tracks, with one of the at least two sensors being embedded in one planar section of the first continuous track and another of the at least two sensors being embedded in another planar section of the first continuous track, and wherein another two of the plurality of sensors are embedded in a second of the pair of continuous tracks, with one of at the least two other sensors being embedded in one planar section of the second continuous track and another of the at least two sensors being embedded in another planar section of the second continuous track.

* * * * *